(12) United States Patent
Wong et al.

(10) Patent No.: US 7,071,474 B2
(45) Date of Patent: Jul. 4, 2006

(54) METHODS AND APPARATUS FOR TUNING SCINTILLATION DETECTORS

(75) Inventors: Wai-Hoi Wong, Houston, TX (US); Hongdi Li, Pearland, TX (US); Jorge Uribe, Houston, TX (US); Yaqiang Liu, Houston, TX (US); Hossain Baghaei, Sugarland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 115 days.

(21) Appl. No.: 10/743,565

(22) Filed: Dec. 22, 2003

(65) Prior Publication Data

US 2004/0188624 A1   Sep. 30, 2004

Related U.S. Application Data

(60) Provisional application No. 60/435,918, filed on Dec. 20, 2002.

(51) Int. Cl.
*G01T 1/164* (2006.01)

(52) U.S. Cl. .............................. 250/363.09; 250/252.1

(58) Field of Classification Search .......... 250/363.09, 250/363.02, 363.03, 363.04, 363.06, 363.07, 250/367, 368, 369, 252.1, 370.11
See application file for complete search history.

(56) References Cited

U.S. PATENT DOCUMENTS

| | | | |
|---|---|---|---|
| 4,033,884 A | 7/1977 | Lorch et al. ................. | 250/496 |
| 4,256,960 A * | 3/1981 | Snider ....................... | 250/252.1 |
| 4,272,677 A | 6/1981 | Berthold et al. ............ | 250/252 |
| 4,424,446 A | 1/1984 | Inbar et al. ............... | 250/363 S |
| 4,517,460 A | 5/1985 | Meulenbrugge et al. . | 250/252.1 |
| 4,582,995 A | 4/1986 | Lim et al. ................. | 250/363 S |
| 4,588,897 A | 5/1986 | Inbar et al. ............... | 250/363 S |
| 4,647,779 A | 3/1987 | Wong ....................... | 250/363 R |
| 4,677,299 A | 6/1987 | Wong ....................... | 250/363 S |
| 4,733,083 A | 3/1988 | Wong ....................... | 250/363 S |
| 4,755,679 A | 7/1988 | Wong ....................... | 250/363 S |
| 4,764,678 A * | 8/1988 | Yamakawa .................. | 250/369 |
| 4,868,392 A | 9/1989 | Wong ....................... | 250/363.03 |
| 4,883,966 A | 11/1989 | Wong ....................... | 250/363.02 |
| 5,237,173 A | 8/1993 | Stark et al. ............... | 250/252.1 |
| 5,272,344 A | 12/1993 | Williams .................. | 250/363.03 |
| 5,319,204 A | 6/1994 | Wong ....................... | 250/363.03 |
| 5,373,161 A | 12/1994 | Tararine et al. ........ | 250/363.09 |
| 5,384,699 A | 1/1995 | Levy et al. ............. | 364/413.13 |
| 5,410,153 A | 4/1995 | Ferreira .................. | 250/363.09 |
| 5,421,215 A | 6/1995 | Cure et al. .............. | 73/864.53 |
| 5,449,897 A | 9/1995 | Bertelsen et al. .......... | 250/207 |
| 5,451,789 A | 9/1995 | Won et al. ............... | 250/363.03 |

(Continued)

OTHER PUBLICATIONS

Badawi et al., "A comparison of normalization effects on three whole-body cylindrical 3D PET systems," *Phys. Med. Biol.*, 45:3253-3266, 2000.

(Continued)

*Primary Examiner*—David Porta
*Assistant Examiner*—Faye Polyzos
(74) *Attorney, Agent, or Firm*—Fulbright & Jaworski LLP

(57) ABSTRACT

Methods and apparatus for tuning scintillation detectors. An output of a first light is equalized with an output of a neighboring, second light. The outputs are measured by one or more light detectors shared by the first and second lights. Outputs of a plurality of light detectors are equalized using the equalized output of the first light.

48 Claims, 7 Drawing Sheets

U.S. PATENT DOCUMENTS

| | | | | |
|---|---|---|---|---|
| 5,453,610 | A | 9/1995 | Gibbons | 250/207 |
| 5,453,623 | A | 9/1995 | Wong et al. | 250/363.03 |
| 5,491,342 | A | 2/1996 | Lim et al. | 250/363.09 |
| 5,525,794 | A | 6/1996 | Gibbons | 250/207 |
| 5,677,536 | A | 10/1997 | Vickers | 250/363.09 |
| 5,825,031 | A | 10/1998 | Wong et al. | 250/363.03 |
| 6,091,070 | A | 7/2000 | Lingren et al. | 250/370.09 |
| 6,121,619 | A | 9/2000 | Johnsen et al. | 250/369 |
| 6,140,650 | A | 10/2000 | Berlad | 250/363.09 |
| 6,310,349 | B1 | 10/2001 | Wong | 250/363.09 |
| 6,342,698 | B1 | 1/2002 | Stark | 250/363.09 |
| 6,452,164 | B1 * | 9/2002 | Andarawis et al. | 250/252.1 |
| 6,835,935 | B1 * | 12/2004 | Engdahl et al. | 250/363.09 |

OTHER PUBLICATIONS

Badawi et al., "Algorithms for calculating detector efficiency normalization coefficients for true coincidences in 3D PET," *Phys. Med. Biol.*, 43:189-205, 1998.

Defrise et al., "A normalization techniques for 3D PET data," *Phys. Med. Biol.*, 36(7):939-952, 1991.

Geworski et al., "Multicenter comparison of calibration and cross calibration of PET scanners," *J. Nucl. Med.*, 43(5):635-639, 2002.

Huber et al., "Characterization of a 64 channel PET detector," *IEEE Transactions on Nuclear Science*, NS-44, 1197-1201, 1997.

Matheoud et al., "Changes in the energy response of a dedicated gamma camera after exposure to a high-flux irridation," *Phys. Med. Biol.*, 44:N129-N135, 1999.

Moses and Derenzo, "Design studies for a PET detector module using a pin photodiode to measure depth of interaction," *IEEE Transactions on Nuclear Science*, NS-41, 1441-1445, 1994.

Reist et al., "Study on the stability of the calibration and normalization in PET and the influence of drifts on the accuracy of quantification," *Eur. J. Nucl. Med.*, 15(11):732-735, 1989.

Uribe et al., "Effect of photomultiplier gain-drift and radiation exposure on 2D-map decoding of detector arrays used in positron emission tomography," *IEEE Nuclear Science Symposium and Medical Imaging Conference Record*, San Diego, CA, Nov. 6-10, 2001.

Yao et al., "Pre-processing variance reducing techniques in multispectral positron emission tomography," *Phys. Med. Biol.*, 42:2233-2253, 1997.

* cited by examiner

METHODS AND APPARATUS FOR TUNING SCINTILLATION DETECTORS

This application claims priority to, and incorporates by reference, U.S. Provisional Patent Application Ser. No. 60/435,918, which was filed Dec. 20, 2002.

STATEMENT AS TO RIGHTS TO INVENTIONS MADE UNDER FEDERALLY-SPONSORED RESEARCH AND DEVELOPMENT

Aspects of this invention were made with grants from the National Institutes of Health (NIH NCI RO1 CA58980; NIH NCI RO1 CA76246; NIH NIBIB RO1 EB001038-04). The Government may have certain rights in this invention.

BACKGROUND OF THE INVENTION

1. Field of the Invention

The invention relates generally to the field of Positron Emission Tomography (PET). More particularly, the invention relates to PET detectors. Even more particularly, one implementation of the invention relates to tuning a PET detector.

2. Discussion of the Related Art

In current clinical PET cameras, there are 1000 or more photomultipliers (PMT) in the detector system. Even a less-complicated gamma camera has many dozens of PMTs. The output of one PMT can vary by 3–5 times from the next PMT for the same detected energy. Image quality and resolution are dependent on the proper equalization of all the PMT outputs; the equalization can be performed by adjusting (manually or electronically) the amplification gain of an amplifier following each PMT and/or by adjusting the high-voltage level supplied to each PMT so that the amplifier outputs for all the PMT are the same for the same energy detected in scintillation detectors. The conventional equalization process (photo-peak pulse-height tuning) for hundreds or thousands of PMTs is very tedious and time consuming. Furthermore, even after an equalization, a PMT output (gain) can change later with many environmental factors such as room temperature, patient load, short-term and long-term radiation exposure, time, etc. Furthermore, these gain changes are different for individual PMTs. A typical PET system-wide PMT-gain adjustment takes many hours (a long down time for a clinical camera), and it is usually performed once every few weeks or every few months. Hence, optimal image quality may not be achieved for all the patients between system equalizations. Furthermore, if one PMT suddenly produces undesirable results such as having gain drop significantly, say, at noon, all the patients imaged in the afternoon will be suboptimal (or useless) without any prior warning.

In sum, conventional PMT equalization methods suffer from several shortcomings, one of the most prevalent being the inability to equalize PMTs in a timely fashion so that the resulting images are more consistent in quality. The referenced shortcomings are not intended to be exhaustive, but rather are among many that tend to impair the effectiveness of previously known techniques concerning PMT tuning methods; however, those mentioned here are sufficient to demonstrate that methodology appearing in the art have not been altogether satisfactory and that a significant need exists for the techniques described and claimed herein.

SUMMARY OF THE INVENTION

There is a need for the following embodiments. Of course, the invention is not limited to these embodiments.

In one respect, the invention involves a method for tuning scintillation detectors. An output of a first light is equalized with an output of a neighboring, second light. The outputs are measured by one or more light detectors shared by the first and second lights. Outputs of a plurality of light detectors are equalized using the equalized output of the first light.

In another respect, the invention involves an apparatus. It includes a first light neighboring a second light, one or more PMTs shared by the first and second lights, a high-frequency pulser with programmable pulse width or pulse height coupled to the lights, and a data acquisition computer coupled to the pulser and configured to control the pulser to adjust a pulse width or pulse height of the second light so that its light output is equalized with a light output of the first light.

The terms "a" or "an," as used herein, are defined as one or more than one, unless the specification explicitly limits the meaning otherwise. The term "plurality," as used herein, is defined as two or more than two. The term "coupled," as used herein, is defined as connected, although not necessarily directly, and not necessarily mechanically. The term approximately, as used herein, is defined as at least close to a given value (e.g., preferably within 10% of, more preferably within 1% of, and most preferably within 0.1% of). The variables n and m, as used herein, denote positive integers. The term sector-sharing denotes the sharing of portions of an area or object. An exemplary sector-sharing arrangement is quadrant-sharing (see U.S. Pat. No. 5,319,204, which is incorporated herein by reference). The term light detector, as used herein, denotes an apparatus which detects the presence of radiation particles. An exemplary light detector is a photomultiplier tube (PMT).

Other features and associated advantages will become apparent with reference to the following detailed description of specific embodiments in connection with the accompanying drawings.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein like reference numerals (if they occur in more than one view) designate the same or similar elements. It should be noted that the features illustrated in the drawings are not necessarily drawn to scale.

DETAILED DESCRIPTION

Figure 1:
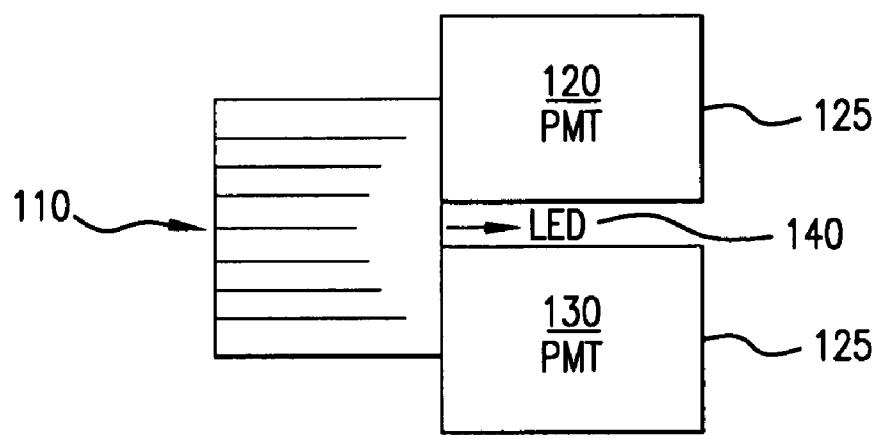
FIG. 1 shows the placement of an LED relative to a group of PMTs, an embodiment of the invention.

The invention and the various features and advantageous details thereof are explained more fully with reference to the nonlimiting embodiments that are illustrated in the accompanying drawings and detailed in the following description. Various substitutions, modifications, additions and/or rearrangements within the spirit and/or scope of the underlying inventive concept will become apparent to those of ordinary skill in the art from this disclosure.

PET scans are very expensive; currently, some patient scans may cost $4,000. The PET tracer injection may cost $600 per dose. It is very important to provide the highest quality image for such an expensive study and to provide for the best patient care. It is also important not to waste a scan when the camera is not functioning properly. The quality-assurance technology presented herein provides an easy and automatic way to achieve these goals. The technology also enables a PET system to be tuned almost instantaneously after component replacement in the detector module, thereby reducing camera down-time that is very expensive.

This disclosure discusses an ultra fast PMT tuning technique that may equalize the gains of a thousand PMTs in as little time as one minute or less without human involvement and without using radioactivity so that, before each patient scan, the entire detector system can be completely tuned. This assures optimal image quality for each patient and provides a warning for any sudden mishap in the detector system before scanning each patient.

Long-term PMT stability and decoding-resolution studies have been conducted, and it was found that there is (a) a long-term ambient PMT-gain variation (5–10% in 100 days), which can be recovered by a system-wide tuning every few weeks or months as in current commercial PET or gamma cameras, and (b) a short-term (daily) variation due to changes in temperature and the level of radiation exposure in the last few hours, which is as large or even larger than the long-term variations in 100 days. This short-term variation cannot be compensated by a re-tuning every few weeks or months. The PMT gain variation due to short-term radiation exposure has been reported by another study, and uncorrected PMT gain-drifts degrade crystal-position decoding and, hence, image resolution. This resolution degradation is especially harmful in ultrahigh-resolution PET systems.

Hence, an instantaneous automated PMT tuning methodology is especially important for ultrahigh resolution PET systems. The methods described herein are 30–100 times faster than the traditional nuclear-counting technique that measures the pulse height of gamma-ray signals using a certain test/reference radioisotope.

In one embodiment, a set of light-emitting diodes (LEDs) is used. Each PMT has a variable-gain amplifier (VGA) connected to its output. Each VGA can be addressed, and its amplification gain can be controlled by a data acquisition computer. If the gain-adjustment dynamic range of one VGA is not enough to obtain the desired amplification gain, then one or more additional VGAs may be added in series. Since the total gain is the PMT gain multiplied by the electronic amplifier gain, the PMT gains may be equalized either by changing the gain of the VGA to have the same output for the whole system, by changing the gain of the PMT to have the same output for the whole system, or by changing both PMT and VGA gains to have a same output for the whole system. The PMT gain can be changed by adjusting the PMT's high voltage power supply. In one embodiment, each time, only one LED in the detector head (with many PMTs) is turned-on for tuning the neighboring PMTs of that LED. The LED is driven by a shared high-frequency pulse generator (100–1000 KHz) with a programmable pulse width (and/or pulse height) controlled by the data acquisition computer, so that each LED can emit a different amount of light as determined by the computer.

All LEDs have two problems that previously prevented them from being used directly for PMT tuning, especially for PET: (i) the light output can vary by more than 2 times between different LEDs even though the driving signals/power are identical; hence, it is not possible to directly generate the same reference light level from each LED in the LED network for tuning all the PMTs in the whole detector head to the same output level, (ii) the LED light output is very sensitive to temperature change, and different LEDs respond differently to temperature.

In this disclosure, techniques that bypass these LED difficulties are presented. These problems may be bypassed by a fast, dynamic light-output control for all of the LEDs in the network so that all of the LEDs will emit the same reference light level for equalizing all the PMT gains. Once the critical light-output variation problem is solved, the LEDs can be used for very fast PMT tuning at least because of two important LED attributes: higher pulse rates and a symmetric light output distribution about the mean light output.

LEDs can be pulsed at a much higher repetition rate than the practical detection rate of the traditional gamma-ray detection-tuning method (10× or more). Since the LED data can be generated and collected at least 10× faster, the tuning time can be reduced by 90%. Secondly, LED light output distribution has a symmetric gaussian shape about the reference light-output level while that of gamma-ray detection signal is very asymmetric. The symmetry of LED signal distribution is exploited by techniques of this disclosure so that the acquired data from the PMT can be used 10× more efficiently than the traditional gamma-ray detection tuning method, contributing to a total of 100× shorter data-acquisition and processing time.

Preliminary data shows that 1000 PMTs in a PET camera can be tuned in one minute or less instead of the 2–6 hours that it takes in current commercial PET systems. The same method, or portions of it, can also be used for gamma cameras or other instruments to speed up the tuning process, as will be understood by those of ordinary skill in the art. Since an LED is driven electronically and no radioactivity is needed as in the traditional tuning method, the whole 1-minute process can be performed automatically without human intervention when the next patient is being loaded.

In one embodiment, a set of LEDs is used. For most scintillation detectors, only true-blue LEDs (or whatever true-color LED is close to the color of the scintillation light) may be used for matching the photo-characteristics of PMTs and scintillation crystals. A true-color LED is a LED that emits optical photons that are very similar in energy values or wavelengths. Non-true color LEDs are not preferred although they may be used. The percentage of wavelengths emitted from non-true-color LEDs may change more drastically as the input current of the LEDs changes.

Figure 2:
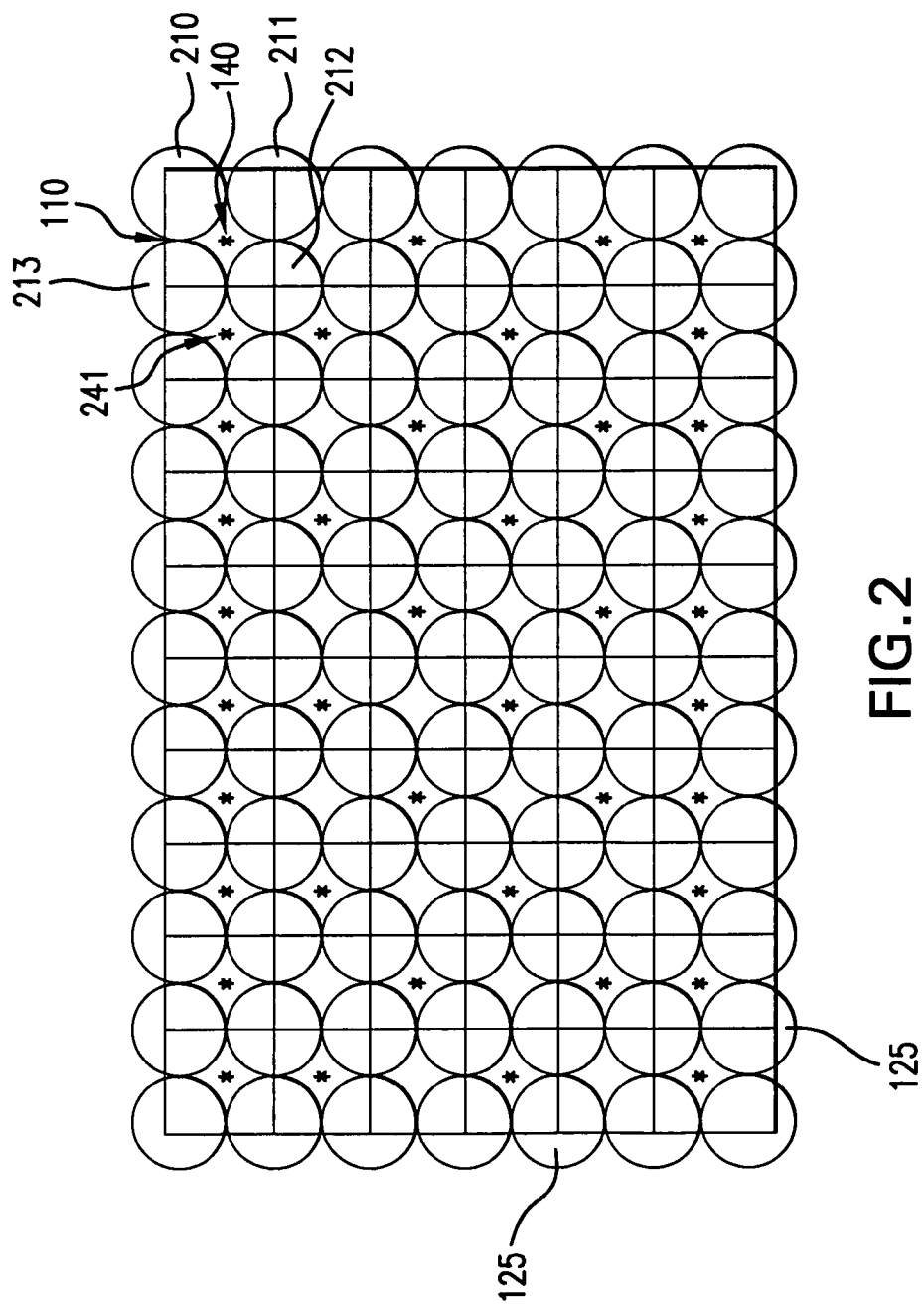
FIG. 2 shows a detector module containing LEDs, an embodiment of the invention. Each square is a crystal array containing many scintillation crystals, each circle is a PMT, and each star is an LED.

FIG. 1 and FIG. 2 show an example of LED placement in an exemplary LED automatic tuning scheme for a PMT-quadrant-sharing (PQS) detector module. As shown in FIG. 1, an LED 140 may be placed in the space between 4-PMT group 125 in the detector module. FIG. 2 shows a different view of a detector module containing LEDs, an embodiment of the invention. Each square 110 is a crystal array containing many scintillation crystals, each circle is a PMT 125, and each star is an LED 140. Although the crystals are shown as squares and the PMTs as circles, those of ordinary skill in the art will recognize that other shapes may be utilized (e.g., the PMTs may be square).

The LED light is directly injected into the center of a crystal array 110 from the PMT coupling side and distributed by the crystal array 110 back into the four neighboring decoding PMTs 125. In one embodiment, no LED light goes to the PMT side wall directly. The LED light may also be guided to the center of the crystal array 110 through a light pipe, light guide, or optical fiber connected to the crystal array 110. In another embodiment of the invention, a bundle of optical fibers may be coupled to an LED at one of the optical fibers, and the other end of the optical fibers may be located in the LED positions shown in FIGS. 1 and 2.

To check that the LED light is injected directly to the center of the crystal array, one may illuminate the crystal array 110 using a gamma source and generate a crystal decoding map which shows the locations of the crystals in relation to the gamma source and then pulse the LED 140 to get an LED map using the same data acquisition method. By comparing the two maps, it is possible to see if the location of the center crystal and the LED 140 in the two maps coincide. This determines if the LED 140 is properly centered.

A positive result of injecting all the LED light into the center of a crystal array 110 and then collecting the LED light by neighboring PMTs 210–213 is that the signals collected not only include the PMT gain but also include the light-coupling efficiency between PMTs 210–213 and crystals 110 (an optical grease/glue may be used to optically couple the crystals 110 to the PMTs 210–213, and there may be air bubbles in the coupling that reduce optical efficiency). A PMT channel with poor optical coupling would also need a higher electronic gain compensation, similar to having a lower gain PMT.

Figure 3:
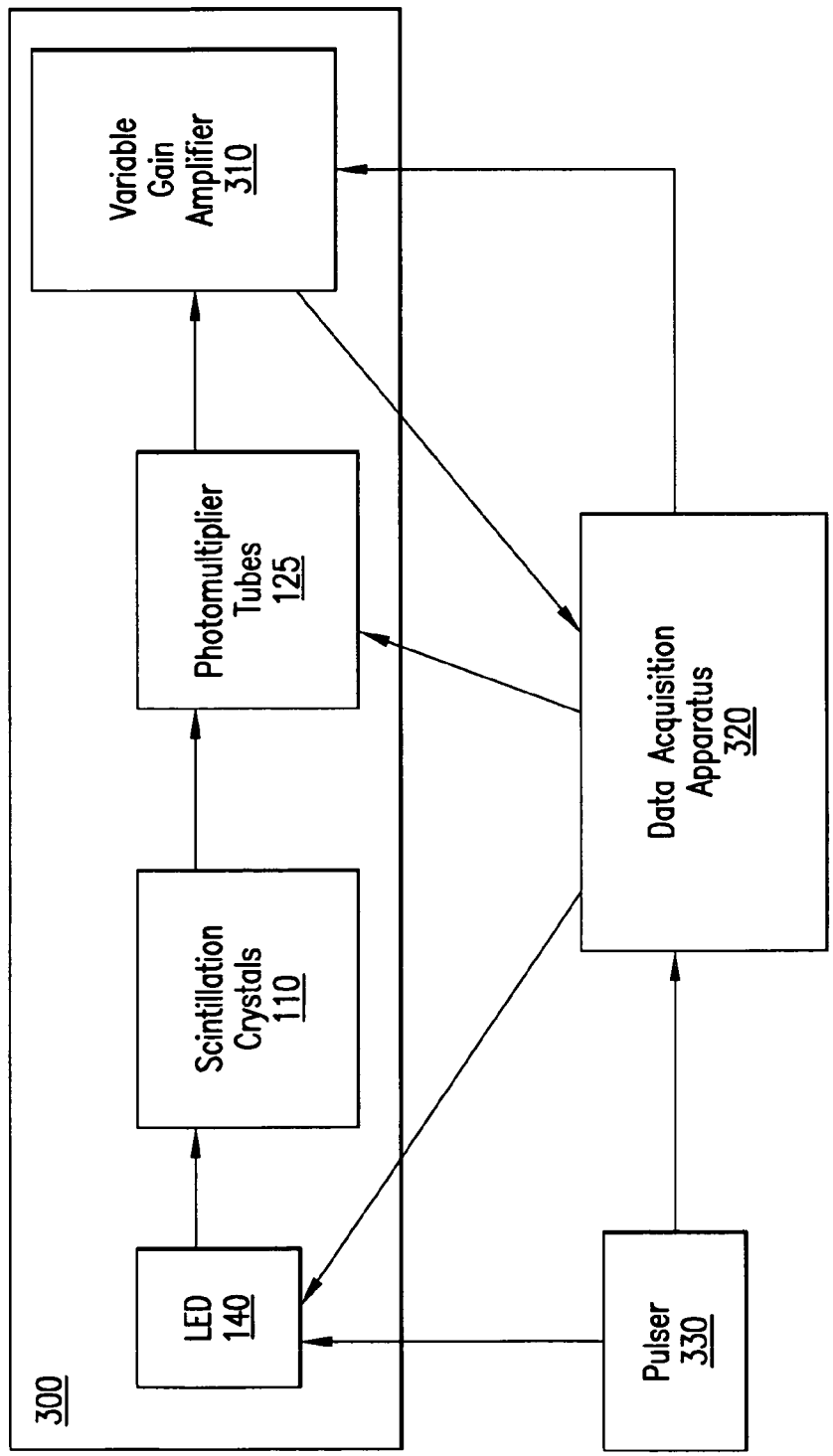
FIG. 3 is a flow chart detailing the steps of an embodiment of the invention.

As shown in FIG. 3, the output of each PMT 125 is connected to a variable-gain amplifier (VGA) 310. Each VGA 310 can be addressed and its gain controlled by the data acquisition apparatus 320 (e.g., a computer). In the same way, each PMT 125 may be controlled by the data acquisition apparatus 320 as well. In this case, the total gain for a PMT channel is the PMT gain (GPMT) multiplied by the electronic amplifier gain ($G_{vga}$):

Total gain for a PMT channel ($G_c$)
$=G_{PMT}*G_{vga}*$Optical coupling efficiency  (Eq. 1), The PMT gains may be equalized by changing the gain of the VGA to the same output for the whole system. Alternatively, both the PMT gain and VGA gain may be changed, as the PMT gain may be adjusted by changing the PMT's high voltage supply. Another way to equalize the PMT gains is by changing the PMT gain, though this may be useful only if the dynamic range of the PMT gain is large enough.

In one embodiment, at any one time, only one LED 140 in the module (or detector head) is turned-on. The LED 140 may be driven by shared high-frequency pulser 330 (e.g., 100–1000 KHz) with programmable pulse width (and/or pulse height) controlled by the data acquisition apparatus 320, so that each LED 140 can emit a different amount of light as determined by the data acquisition apparatus 320.

The total (integrated) LED-light output ($L_{LED}$) of each pulse (number of photoelectrons collected by the PMT) should be adjusted to be comparable to that of the targeted gamma rays, with no electronic signal overflow within the target range of the amplifier, integrator, or A/D converter. The signal amplitude (voltage level) or integrated signal strength (integrated electrical charge of the LED) should be approximately in the range of the signal strength of the signal produced by the energy of a target gamma-ray so that one may use the same electronics for processing the LED-signal as well as for processing gamma ray signals. No extra electronics may be needed for the tuning to save cost as well as space. If the LED signal is too large or too small (out of detecting range), the electronics may not be able to handle them.

For each pulse, the integrated signal amplitude ($V_{LED}$) from the LED for each PMT channel will be:

$V_{LED}=G*L_{LED}=(G_{PMT}*$Optical coupling efficiency$)$
$*G_{vga}*L_{LED}$  (Eq. 2)

The same data-acquisition electronics can be used to perform PMT equalization in order to save cost. Unlike the real scintillation signal generated in the scintillation crystals by a gamma ray, the LED light has a much slower rise time. Hence, the fast triggering circuit for initiating the integration of each gamma ray or LED signal may not be triggered by the LED signal. Fortunately, since a pulsing circuit generates the LED light pulse, the same pulser can be used to enable or trigger the signal integration (processing) of the LED signal synchronously.

The total light output of an LED in the middle of a 4-PMT group may be tuned by adjusting the pulser, which changes the pulse width and pulse amplitude, so that the total light output for each pulse for this LED is that of the same as that of the adjacent LED tuned immediately before. This neighboring LED light-output tuning process may be performed as follows:

Since two neighboring LEDs each have their light going into a common PMT, any one of the two PMTs between two neighboring LEDs (FIG. 2) may be used as a reference PMT. This pair of shared PMTs (e.g. PMTs 212 and 213) may be used as a temporary or local reference for two neighboring LEDs (e.g. LEDs 140 and 241) regardless of whether the two PMTs' gains have been equalized or not. Hence, two neighboring LEDs may be tuned to generate the same amount of light to shine on the same common pair of PMTs. Any adjacent pair of PMTs can be used as a temporary reference to tune the outputs of two adjacent LEDs. Using this neighboring-LED tuning method, the outputs for all of the LEDs in the module can be tuned just before a PMT tuning session.

The individual settings of the pulse widths and pulse amplitudes for all the LEDs may be measured in seconds, and these settings may be recorded in a LED-setting table stored in a data-acquisition apparatus (computer) 320 just before the PMT-equalization process. Immediately following the LED tuning, individual PMT equalization may begin. The data-acquisition apparatus 320 may turn-on a first LED, adjusting the LED output according the setting defined in the LED-setting table for this LED, while keeping the rest of the LEDs turned off. The gains of the four PMTs surrounding this LED are equalized. The next LED will then be turned-on, and the process is repeated.

In one embodiment, a different tuning sequence may be used. The LED-setting table does not need to be generated beforehand. A first LED may be turned-on with an initial setting to equalize its associated four PMTs. Immediately afterwards, the first LED is turned off, a second LED is turned-on, and the output of the second LED is tuned by changing the pulse width and amplitude to match that of the first LED using the common pair of PMTs as a reference point. After finding the appropriate setting for the second LED, the gains of its associated PMTs can be equalized. This process is repeated for the remaining PMTs.

Since the light outputs of all the LEDs are tuned immediately before the PMTs are equalized, the drifting of LEDs' light output from temperature variation is negligible during the PMT equalization process because the thermal effect of warming or cooling the detection system from room temperature takes 1–2 orders of magnitudes longer than the time needed to equalize all of the PMTs.

Generally, the sensitivity response of a PMT is not uniform across the entrance optical window (photocathode). Hence, each of the 4 quadrants or 2 halves of the entrance window may have a different sensitivity or gain. This variability may be considered in designing an LED light-output tuning method. The higher sensitivity quarter or half of a PMT generates a larger amount of signal than a lower sensitivity quarter or half, although the two adjacent LEDs have the same light output. To measure the regional sensitivity variations in each PMT, all of the PMTs in the whole detector module or system may be equalized a first time (and only once) by the traditional nuclear-photopeak pulse-height matching technique.

Figure 4:
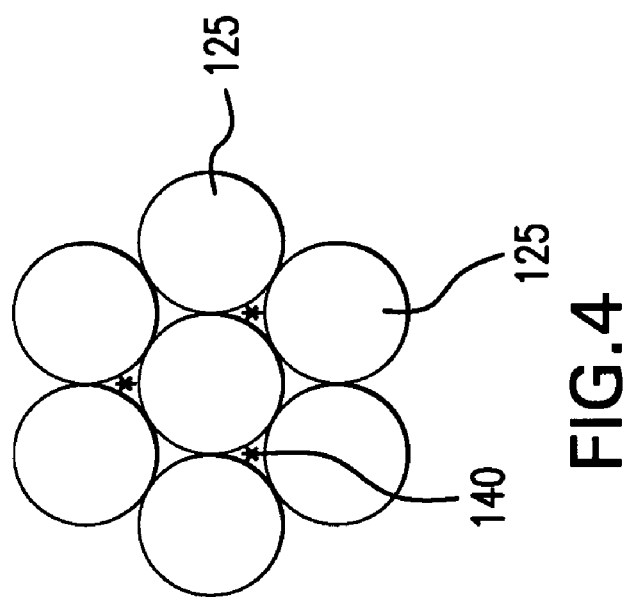
FIG. 4 shows an example of a hexagonal close-packing (honeycomb) of PMTs and LEDs in a gamma camera, an embodiment of the invention.

The nuclear-counting equalization is performed using the variable-gain amplifier (VGA) connected to the output of each PMT. Each VGA may be addressed and its gain controlled by the data acquisition apparatus 320 until preset equalization conditions are met. After the traditional nuclear-counting equalization step, a few crystals situated inside each quarter of the shared PMTs may be selected, and the average photo-peak pulse-height of those crystals indicates the sensitivity of the quarter. Data for sensitivity correction does not need to correspond to quadrants; it can be, e.g., a ½, ⅓ or ⅙ fractional sector or a fractional-sensitivity-weighted-sum of all the sectors, depending on the PMT packing arrangement, e.g., the hexagonal close-packing (honeycomb) of PMTs 125 in gamma cameras (FIG. 4), and depending on whether there is a light guide between the crystal arrays and the PMT arrays.

With this data, a lookup-table may be created in the data acquisition apparatus 320 to store the measured sensitivity of each quadrant or the weighted-sum-sector sensitivity of the PMTs. This regional sector-lookup table may be used to generate a regional-sensitivity correction factor to the LED light-output tuning control for all subsequent LED tuning. Setting up a permanent PMT regional sector-lookup table may take a few hours, much like current PMT tuning in commercial PET, but subsequent PMT tunings using the LEDs would take only 1–2 minutes.

Figure 5:
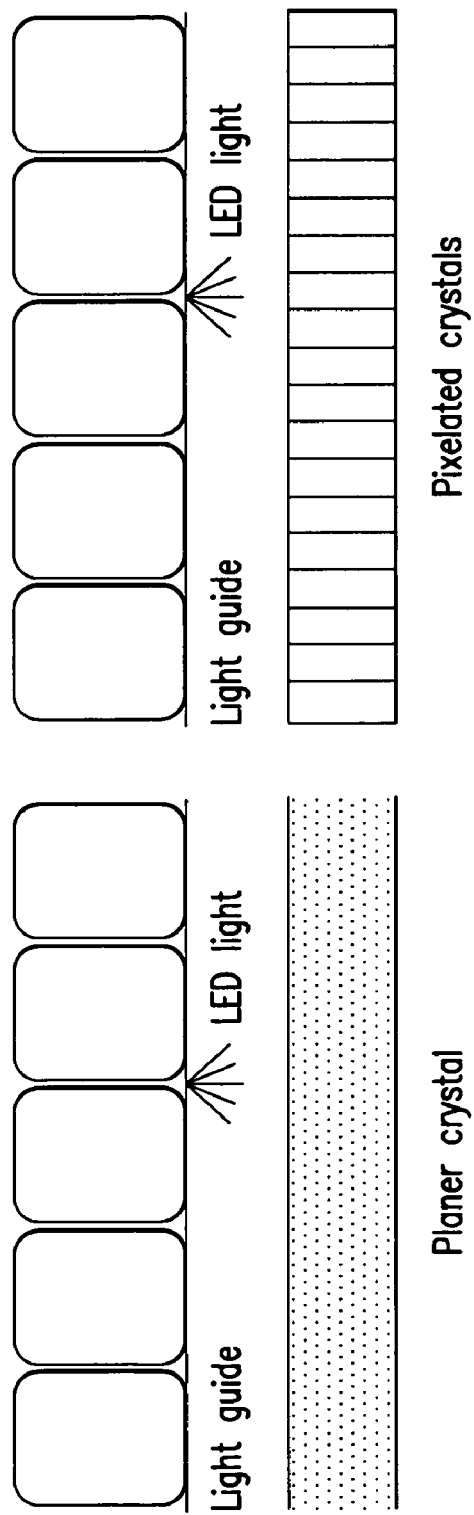
FIG. 5 shows an example of LED light distribution using a light guide.

LED tuning methods of this disclosure may also be used for a wide array of detector setups including but not limited to the PMT-Quadrant-Sharing block detector designs with or without light guides. In one embodiment, the LED tuning method may be used for a detector with scintillation crystals coupled to a continuous light guide such as a detector found in a gamma camera or in a pixelated crystal detector. As shown in FIG. 5, with the light guide, the LED light may be equally distributed to PMT-m and PMT-n. In other words, PMT-m and PMT-n should show the same LED energy peak if their respective gains are balanced. In this design, using a large area light guide, the regional weighted-sum sector-lookup table is needed because when an LED is pulsed, its light is not emitted through only one sector/quadrant, as it does in the quadrant-sharing detectors. Instead, it is transmitted to all of the sectors of a PMT, and the resulting LED light measurements are affected by the different geometrical efficiencies or weights of each sector.

The regional sector-lookup table may also be measured externally on a separate calibration apparatus that simulates the detector design (i.e. quadrant sharing or hexagonal-sharing with light guide). In one embodiment of this calibration setup, only one reference LED is placed in a fixed position to simulate an actual LED position in the detector module. The PMT sensitivity is measured in a first defined position with the single pulsing LED. The PMT is turned about its center by a fixed degree to simulate the geometry of the PMT with other LEDs in the detector system (i.e. 90°, 60°, or 30°) and the sensitivity is measured again. This process is repeated until the PMT has returned to its original position. Thus, the anisotropic sensitivity of the PMT may be determined to form the regional sector-lookup table for the PMT. Each PMT may be mapped this way before its installation into the detection system.

Figure 6A:
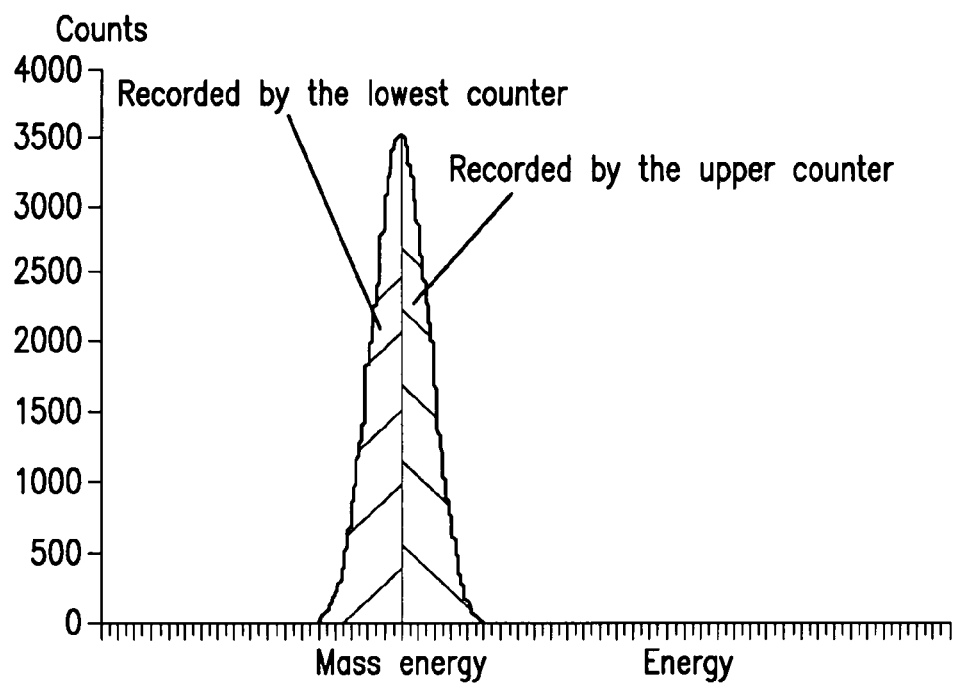
FIG. 6a is a graph of a symmetric Gaussian-shape pulse-height distribution spectrum of a LED light signal, which is useful in embodiments of the invention.
Figure 6B:
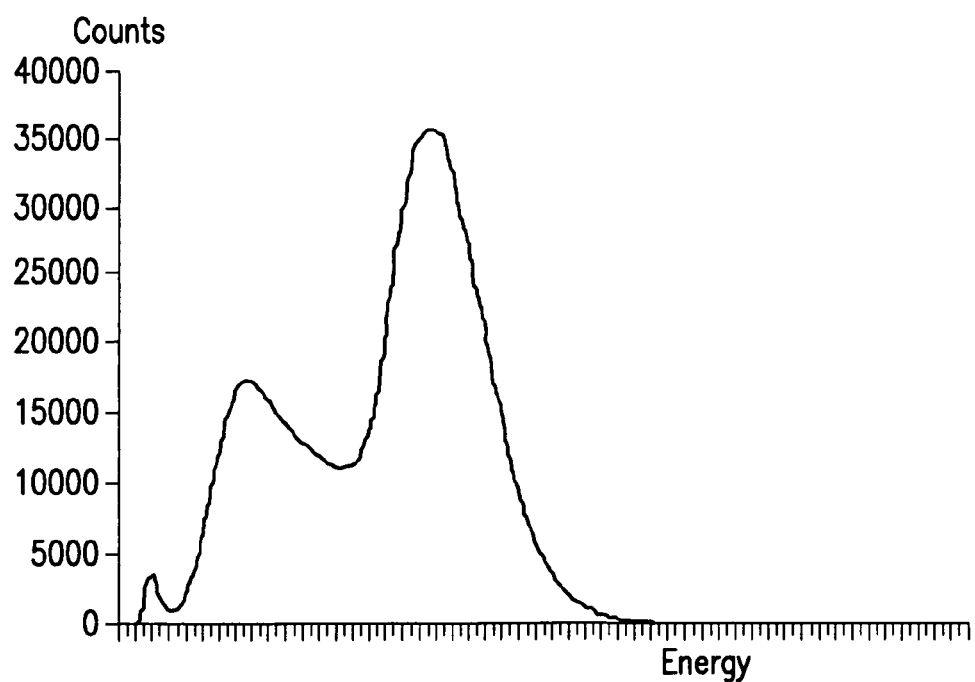
FIG. 6b is a graph of a pulse-height distribution spectrum of a gamma-ray, which is useful in embodiments of the invention. The main peak at higher energy levels comes from the reference gamma-ray. The events with energies below the main peak are scattered gamma-ray events.

An important advantage of LED tuning is that the LED light-signal pulse-height energy distribution spectrum (PHS) detected by the detection system is a narrow, symmetrical Gaussian about the mean energy, without the low-energy scatter events of a gamma-counting PHS (FIG. 6A). However, even though the LED may be constantly driven by the same electrical input-pulse shape, the PMT detected light output for each LED pulse may have statistical variations. One pulse may yield a higher detected light output than the mean output, as defined by the electrical input-pulse shape, while a second pulse may yield a lower light output than the mean output. When many pulses are collected, a symmetric energy distribution or energy spectrum is obtained. In the traditional nuclear counting/detection method, in addition to statistical variation, there is a lower energy component or scatter component in the detected energy spectrum (FIG. 6B) because the scintillation crystals do not always convert all the incident gamma-ray energy into light energy. For a fair fraction of the time, the incident gamma rays convert only a fraction of their incident energy into light energy, with the remaining energy escaping the crystals as a scattered gamma ray. Hence, the detected gamma-ray PHS is not symmetric about the main signal peak (FIG. 6B).

Since LED light output is already a light signal instead of gamma rays, its light signal does not need to be converted into light by the scintillation crystals. Without going through the imperfect scintillation-conversion process, the detected LED signal only has a statistical variance that is symmetric.

This simple LED feature may be exploited to greatly increase the speed of equalization. Because of the symmetric shape of the energy distribution, as few as two counters may be used, with one upper counter to count the number of events above a reference pulse height (e.g., the designated mean energy in FIG. 6A) and a lower counter to count events below the reference mean. A simple, continuous comparison of the two counters will guide the gain auto-adjustment of the VGA until both counters have about the same number of events. For example, if the upper counter has more counts than the lower counter, that means the PMT gain is too high. The amplification gain of the PMT and/or its VGA may then be reduced. Then, the two counters may be restarted from zero for the next iterative check to determine if the two counters match after the amplification change. If the lower counter has more counts than the upper counter, that means the PMT gain is too low. The VGA/PMT gain may be increased by a step, and the two counters restart from zero again.

Hence, in one embodiment, all of the detected data may be fed into only two registers, which means that the statistics accumulate very fast in each register. It takes only a short time to accumulate very good statistics for reliable decision-making.

In the conventional nuclear-counting method, with an asymmetric PHS, such a two counter comparison is not feasible, and the full PHS spectrum has to be collected, which means that the collected data have to be split out into many channels/bins that sample/represent the full energy spectrum (a typical PHA spectrum is made of 64-5 12 bins/channels). If there are 100 bins in the PHA, each bin will represent 1% of the spectrum. Since the data are spread over 100 bins (instead of the 2 disclosed here), the statistics in each bin will take a much longer time to accumulate to provide enough statistical accuracy for decision-making. Thirdly, after each accumulation, a data-acquisition computer will have to numerically compare all the bins in the entire PHS to find the energy peak before deciding whether the last VGA gain modification was in the right direction and to determine the magnitude of the next iterative VGA-gain modification. This peak-searching process is much more tedious and time consuming than the two register comparison that may be used here. It would take many more counts with a longer data collection time and a longer computer analysis than the two-channel counter technique allowed by LED tuning.

In one embodiment, the two-register comparison method can be performed in real time with a simple comparator circuit, without involving a processor, thereby reducing overall cost and complexity of the equipment.

Figure 7:
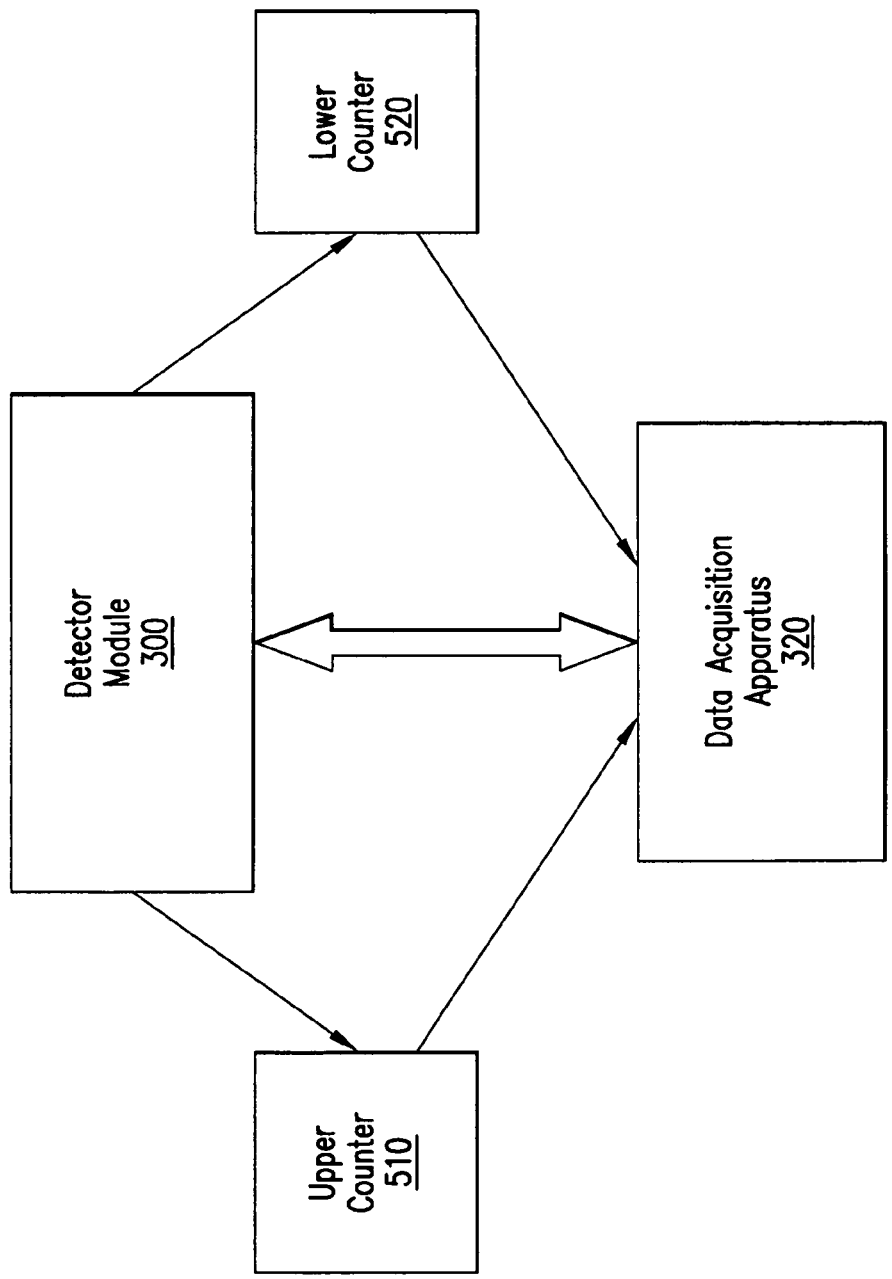
FIG. 7 illustrates the process of assessing PMT equalization, an embodiment of the invention.

One technique to implement a two-counter comparison is as follows. One set of tuning electronics, as shown in FIG. 7, is present in each module 300 for real-time counting of the signal above and below the reference pulse height. If one counter (either one) 510, 520 is full (say, at 10000 counts), the other counter 520, 510 will be immediately compared to a threshold (say, 9990 counts). If the other count is over the threshold, the equalization for a PMT is finished within tuning resolution of 10/10000 or 0.1% allowable error, which is negligible (in other embodiments, different allowable errors may be used); otherwise the PMT equalization needs further adjustment. If the upper counter 510 is full first, the gain is too high. If the lower counter 520 is full first, the gain is too low. The data acquisition apparatus 320 only reads the information of which counter 510, 520 reaches the full status first and whether the equalization needs to be continued. Furthermore, if a camera has 12 detector modules, the auto-tuning of 12 modules can be performed at the same time, which means it will be an additional 12 times faster than a traditional method.

Another issue arises in conjunction with the techniques of this disclosure. Namely, what should the output amplitude be for all of the PMTs? In different embodiment, it may be useful to arrive at an optimal range or optimal value for the output amplitude. In other words, there should be a reference range or a reference value by which to set all the PMT channels. The reference may not need to be perfectly accurate or perfectly reproducible every time because what is more important is the precision of uniformly setting the outputs of all the PMT channels.

In the traditional equalization process using radioisotopes, the known gamma-ray energy of the reference radioisotope are used as the reference, and all of the PMT channels are equalized to produce the same signal amplitude (e.g., 5 volts) for the characteristic/reference gamma ray used.

In this method, there is no reference gamma ray. A different way of establishing a reference range or a reference value is needed for embodiments of this disclosure. There are several ways to achieve this:

(i) Each night, after the completion of the last patient. A radioactive source can be put into the field of view. For each detector module, a stable PMT is chosen as a reference PMT, and signals from several scintillation crystals at the center of the reference PMT may be chosen as reference signals to set the gain of the reference PMT channel. After setting the gain of the reference channel, the light output of the LEDs associated with the reference PMT may be adjusted to the target value at the output of the reference PMT channel. Once the light outputs of these LEDs are set, these LEDs may serve as the reference LED for setting the light levels of all the other LEDs in the module as described earlier for tuning all the PMTs to the reference levels. (Note: the reference PMT may be selected from the gain-adjustment recordlog accumulated from previous equalization procedures). Hence, for each day, the reference may be re-established and all the patient studies for that day will use the same reference setting, as the reference may not need to be perfectly accurate or perfectly reproducible every time because what is more important is the precision of uniformly setting the outputs of all the PMT channels—not the absolute accuracy.

(ii) From a previous equalization record/log, a stable or a "mean" PMT for each detector module may be chosen as a reference channel. The light outputs of the LEDs associated with the reference PMT may be adjusted "with faith" to the target value. The light outputs of these LEDs may be used as reference for setting the light outputs of all the other LEDs in the detector modules as discussed earlier. The outputs/gains for all the PMT channels may then be equalized (eq. 2). A statistical analysis on the gain-change required for all the PMT channels may be performed. If most of the PMT channels required the same percentage change (say a 10% lower gain is needed to get to the target amplitude), the systematic change is a good indication that the reference PMT has in fact changed by that percentage (i.e., the reference PMT-gain has decreased by 10%) instead of being stable. Hence, all of the other PMT channels were "misled" by following the leader (reference PMT). In this case, all the PMT channels in the detector module may be increased by the same percentage (10%) to get back to the true target value.

(iii) A combination of (i) and (ii) may be used.

(iv) The gamma-ray reference source in (i) can also be obtained from patients who have been injected with radiotracers. The reference can be established for each patient just before imaging. The reference can also be established from the last or the first patient of the day.

(v) One independent light detector (inside each detector module) can also be used to tune the light output of the reference LED.

(vi) One temperature-stable light source (inside each module) can also be used as a comparison standard to set the light output of the reference LED. One such light source may have feedback control to cancel any temperature effects.

To summarize some advantages of some of the exemplary techniques of this disclosure: greatly improved tuning techniques are presented. Namely, in a preferred embodiment, an LED method with a two-channel comparison technique represents a much simpler, more accurate method that requires fewer counts. In addition, each LED can be driven 100K–1000K counts/sec, which is much higher than the gamma-ray counting rate per PMT (by 10× or more).

EXAMPLES

The examples should not be construed as limiting the scope of the invention.

LED-equalization for a PQS PET detector with 4 PMTs has been tested. Repeated PMT tuning for the same 4 PMT revealed that equalization can be achieved with errors of ≦1%, which is much more accurate than the traditional nuclear-detection method. Extrapolating from this data, 924 PMT may be equalized in 1 minute. Hence, before each patient study, a complete retuning can be performed during patient-loading time; since the tuning is performed without radioactivity or human intervention, this tuning can be performed automatically.

REFERENCES

Each of the references is hereby incorporated by reference in its entirety.
1. U.S. Pat. No. 6,310,349
2. U.S. Pat. No. 5,825,031
3. U.S. Pat. No. 5,453,623
4. U.S. Pat. No. 5,451,789
5. U.S. Pat. No. 5,319,204
6. U.S. Pat. No. 4,883,966
7. U.S. Pat. No. 4,868,392
8. U.S. Pat. No. 4,755,679
9. U.S. Pat. No. 4,733,083
10. U.S. Pat. No. 4,677,299
11. U.S. Pat. No. 4,647,779
12. Uribe, J., Li, H., Baghaei, H., Aykac, M., Wang, Y., Liu, Y., Xing, T., Wong, W-H. "Effect of Photomultiplier Gain-Drift and Radiation Exposure on 2D-Map Decoding of Detector Arrays Used in Positron Emission Tomography". 2001 IEEE Nuclear Science Symposium and Medical Imaging Conference Record, San Diego, Calif., Nov. 6–10, 2001.
13. Matheoud R, Zito F, Canz C, Voltini F, Gerundini P. "Changes in the energy response of a dedicated gamma camera after exposure to a high-flux irradiation". Phys. Med. Biol., 44, N129–N135, 1999.

We claim:

1. A method for tuning scintillation detectors, comprising:
equalizing an output of a first light with an output of a neighboring, second light, the outputs being measured by one or more light detectors shared by the first and second lights; and
equalizing outputs of a plurality of light detectors using the equalized output of the first light.

2. The method of claim 1, the first and second lights comprising light from optical fibers coupled to a LED.

3. The method of claim 1, the light detectors comprising photomultiplier tubes (PMTs).

4. The method of claim 1, the first and second lights comprising LEDs.

5. The method of claim 4, equalizing the output of the first light comprising adjusting a pulse width or pulse amplitude input of a first LED.

6. The method of claim 5, the pulse width or pulse amplitude used for equalizing the output of the first LED being stored in a memory.

7. The method of claim 6, equalizing outputs of the plurality of light detectors comprising equalizing outputs of n light detectors surrounding the first LED.

8. The method of claim 7, the n light detectors being in a sector-sharing arrangement.

9. The method of claim 8, further comprising applying a sector-sensitivity correction factor to the pulse width or pulse amplitude to generate the equalized output of the first LED.

10. The method of claim 9, wherein the sector-sensitivity correction factor is generated from a sector-lookup table.

11. The method of claim 7, wherein n is 4.

12. The method of claim 7, wherein n is 6.

13. The method of claim 1, equalizing the outputs of the plurality of light detectors comprising adjusting gains of the light detectors.

14. The method of claim 13, adjusting gains comprising adjusting gains of variable-gain amplifiers coupled to the light detectors.

15. The method of claim 1, the first light having a symmetrical pulse-height energy distribution spectrum, and equalizing the outputs of the plurality of light detectors being performed using two registers, a first register counting events above a reference and a second register counting events below the reference.

16. The method of claim 1, further comprising establishing a reference output for one or more of the plurality of light detectors.

17. The method of claim 16, establishing a reference output comprising using an independent light detector or a temperature-stable light.

18. The method of claim 16, establishing a reference output comprising using a radioactive source as a reference.

19. The method of claim 18, the radioactive source comprising a radioactive source injected into a patient.

20. The method of claim 1, further comprising generating a trigger signal for initiating the integration of a gamma ray or a light signal.

21. The method of claim 20, wherein the trigger signal is generated by a pulser of a LED.

22. The method of claim 20, wherein the trigger signal is synchronized with a pulser of a LED.

23. The method of claim 1, further comprising equalizing outputs of a plurality of light detectors using the output of the neighboring, second light.

24. The method of claim 1, further comprising selecting a reference light detector.

25. The method of claim 24, wherein the reference light detector is selected from an equalization log.

26. A method for tuning light detectors, comprising:
equalizing outputs of a first plurality of light detectors using the output of a first light;
equalizing an output of a second light with the output of the first light, the second light neighboring the first light and the outputs of the first and second lights being measured by one or more shared light detectors; and
equalizing outputs of a second plurality of light detectors using the equalized output of the second light.

27. The method of claim 26, the first and second lights comprising light from optical fibers coupled to a LED.

28. The method of claim 26, the first and second lights comprising LEDs.

29. The method of claim 26, the light detectors comprising photomultiplier tubes (PMTs).

30. The method of claim 26, the equalizing of the output of the second light comprising adjusting a pulse width or pulse amplitude input of a second LED.

31. The method of claim 30, the pulse width or pulse amplitude used for equalizing the output of the second LED being stored in a memory.

32. The method of claim 31, the equalizing outputs of the second plurality of light detectors comprising equalizing outputs of n light detectors surrounding the second LED.

33. The method of claim 32, the n light detectors being in a sector-sharing arrangement.

34. The method of claim 33, further comprising applying a sector-sensitivity correction factor to the pulse width or pulse amplitude to generate the equalized output of the second LED.

35. The method of claim 34, wherein the sector-sensitivity correction factor is generated from a sector-lookup table.

36. The method of claim 32, wherein n is 4.

37. The method of claim 32, wherein n is 6.

38. The method of claim 26, the equalizing the outputs of the plurality of light detectors comprising adjusting gains of the light detectors.

39. The method of claim 38, adjusting gains comprising adjusting gains of variable-gain amplifiers coupled to the light detectors.

40. The method of claim 26, the second light having a symmetrical pulse-height energy distribution spectrum, and equalizing the outputs of the second plurality of light detectors being performed using two registers, a first register counting events above a reference and a second register counting events below the reference.

41. The method of claim 26, further comprising establishing a reference output for one or more of the light detectors.

42. The method of claim 41, establishing a reference output comprising using a radioactive source as a reference.

43. The method of claim 42, the radioactive source comprising a radioactive source injected into a patient.

44. The method of claim 41, establishing a reference output comprising using an independent light detector or a temperature-stable light.

45. An apparatus, comprising:
a first light neighboring a second light;
one or more PMTs shared by the first and second lights;
a pulser with programmable pulse width or pulse height coupled to the lights;
a data acquisition computer coupled to the pulser and configured to control the pulser to adjust a pulse width or pulse height of the second light so that its light output is equalized with a light output of the first light.

46. The apparatus of claim 45, wherein the first and second lights comprising LEDs.

47. The apparatus of claim 45, wherein the first and second lights comprising optical fibers coupled to a LED.

48. The apparatus of claim 45, the PMTs being in a quadrant-sharing arrangement.

* * * * *

UNITED STATES PATENT AND TRADEMARK OFFICE
CERTIFICATE OF CORRECTION

PATENT NO. : 7,071,474 B2
APPLICATION NO. : 10/743565
DATED : July 4, 2006
INVENTOR(S) : Wai-Hoi Wong et al.

It is certified that error appears in the above-identified patent and that said Letters Patent is hereby corrected as shown below:

In column 1, lines 13-16, delete
"Aspects of this invention were made with grants from the National Institutes of Health (NIH NCI RO1 CA58980; NIH NCI RO1 CA76246; NIH NIBIB RO1 EB001038-04). The Government may have certain rights in this invention."
and insert
--This invention was made with government support under grant numbers CA058980, CA076246, EB001038, and EB001481 awarded by the National Institutes of Health. The government has certain rights in the invention.-- therefor.

Signed and Sealed this

Eleventh Day of August, 2009

David J. Kappos
*Director of the United States Patent and Trademark Office*